United States Patent [19]

Maggi et al.

[11] 4,369,146

[45] Jan. 18, 1983

[54] METHOD FOR CHLORINATING THE CARBOXYLIC GROUP OF α-AMINOACIDS

[75] Inventors: Rodolfo Maggi; Gian P. Maggi, both of Milan; Giuliano Marcon, Bulciago, all of Italy

[73] Assignee: Chimica Bulciago S.r.l., Bulciago, Italy

[21] Appl. No.: 261,516

[22] Filed: May 7, 1981

Related U.S. Application Data

[63] Continuation of Ser. No. 120,357, Feb. 11, 1980, abandoned.

[30] Foreign Application Priority Data

May 3, 1979 [IT] Italy ............................. 22323 A/79

[51] Int. Cl.$^3$ ............................................ C07C 51/60
[52] U.S. Cl. ............................ 260/544 N; 260/465 D
[58] Field of Search ........... 260/465 D, 544 D, 544 N

[56] References Cited

U.S. PATENT DOCUMENTS 3,925,418 12/1975 Williams et al. ........... 260/544 D X

FOREIGN PATENT DOCUMENTS 1241844 8/1971 United Kingdom .

OTHER PUBLICATIONS

Fieser and Fieser, Advanced Organic Chemistry, Reinhold Publishing Corp., New York (1961) pp. 382–383.

*Primary Examiner*—Dolph H. Torrence
*Attorney, Agent, or Firm*—Browdy & Neimark

[57] ABSTRACT

A method for chlorinating the carboxylic group of α-aminoacids (e.g. hydroxyphenyl-glycine) is described wherein the aminoacid is suspended in an optionally solvate-forming solvent, treated with an excess of gaseous HCl and then with a chlorinating agent having the general formula [$SO_aCl_2.R_1R_2NCHO$] (e.g. $SOCl_2.(CH_3)_2NCHO$).

A typical compound thus obtained is the dioxane hemisolvate of D(−)2-(p-hydroxyphenyl)glycyl chloride hydrochloride.

4 Claims, No Drawings

METHOD FOR CHLORINATING THE CARBOXYLIC GROUP OF α-AMINOACIDS

This is a continuation of application Ser. No. 120,357, filed Feb. 11, 1980, abandoned.

FIELD OF THE INVENTION

The present invention relates to an improved method for chlorinating the carboxylic group of α-aminoacids, particularly p-hydroxyphenylglycine and 2-phenylglycine, as well as of the relevant derivatives.

BACKGROUND OF THE INVENTION

The chlorination of carboxylic group of α-aminoacids by means of the usual chlorinating agents such as $PCl_5$, $PCl_3$, $Cl_2$, $SOCl_2$, etc. often presents synthesis difficulties due both to the steric hindrance and to the presence of various substituents. Among the hardly chlorinatable aminoacids there is for instance included p-hydroxyphenylglycine, since, among other things, the presence of hydroxyl group on the benzene ring considerably disturbs the production of acyl chloride and besides the obtention of the product in crystalline and stable form is difficult, which form is necessary for an effective recovering from the reaction mixture.

Among the many attempts aiming at attaining the chlorination on the carboxylic group of p-OH-phenylglycine, two processes had a certain success, the first of them, which is based on the use of phosgene as the chlorinating agent and described in U.S. Pat. No. 3,925,418 as well as by Brenner and Photaki in Helv. Chimica Acta, 1956, pages 1525–26, is rather complex as it consists in forming a cyclic anhydride and successively cleaving with gaseous hydrogen chloride, and further requires the use of phosgene, which gives rise to noticeable plant problems due to its dangerous nature and corrosivity. The second process is based on the use of chloromethylene-dimethylammonium chloride as the chlorinating agent and is described in the U.S. patent application Ser. No. 29,126 filed Apr. 11, 1979 now U.S. Pat. No. 4,272,454 in the name of same applicants.

SUMMARY OF THE INVENTION

The applicant company, in the course of its studies on the obtention of chlorides of α-aminoacids and particularly of 2-(p-hydroxyphenyl)glycine, has developed a chlorinating process which provides a good and practical novel method for preparing the desired hydrochloride chloroderivatives with high purity.

Such a high purity degree is essential, as the products obtained by this novel process were found to have physico-chemical properties which are suitable for the production of semi-synthetic penicillins and cefalosporins.

The chlorination process according to the present invention involves the use of chlorinating agents of the type

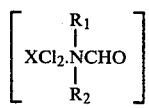

(I)

wherein X can be SO and $SO_2$; $R_1$ and $R_2$ can be, each other independently, low alkyl groups such as $CH_3$, $C_2H_5$ etc., or aryl groups such as $C_6H_5$.

The use of adducts of type (I) has been unexpectedly found to be satisfactory e.g. in the chlorination of 2-(p-hydroxyphenyl)glycine under mild conditions. The type (I) adducts can be prepared by reacting equimolar amounts of $XCl_2$ and $R_1R_2NCHO$ at low temperature. The α-aminoacid, in particular 2-(p-hydroxyphenyl)glycine is suspended in organic solvents and the suspension is treated with hydrochloric acid to give the hydrochloride of the aminoacid. By reacting this suspension with the chlorinating agent of type (I) under mild temperature conditions the acyl chloride is obtained which can easily be recovered from the reaction mixture.

The organic solvents which are suitable to the process according to this invention should have a substantial chemical inertness towards both the adduct (I) and 2-(p-hydroxyphenyl)glycine and further be capable of selectively insolubilizing the desired chlorination product with a high purity degree.

Examples of suitable solvents comprise acetonitrile, tetrahydrofurane, benzene, toluene, n-hexane, dioxane, ethyl acetate, dichloromethane, chloroform, dichloroethane.

The preferred solvent in order to get good yields is dioxane or a mixture of dioxane with one or more listed solvents. It has been found that dioxane has not only a suspending or solubilizing function with respect to 2-(p-hydroxyphenyl)glycine, but also a stabilizing function to the final product due to the formation of a hemisolvate of 2-(p-hydroxyphenyl)glycyl-chloride hydrochloride.

Besides it has turned out that also the use of acetonitrile as the reaction solvent allows one to obtain the chlorinated product firmly solvated with one mole of acetonitrile.

DESCRIPTION OF THE PREFERRED EMBODIMENT

The present invention will now be further described with reference to some embodying examples given for illustrative and non-limiting purposes.

EXAMPLE 1

Preparation of the adduct $[SOCl_2.(CH_3)_2NCHO]$

In a flask equipped with stirrer, thermometer and thermostatic bath 119.2 g (1 mole) of thionyl chloride are charged, cooled to 0° C. and 73.1 g (1 mole) of N,N-dimethylformamide are added under stirring yet maintaining the temperature below 5° C. At the end of the addition the temperature is allowed to rise up to 20° C. and then maintained constant for at least 3 hours.

192 g of a yellow oily liquid which is extremely reactive with atmospheric moisture are obtained.

EXAMPLE 2

Preparation of the adduct $[SO_2Cl_2(CH_3)_2NCHO]$

In a flask equipped with stirrer, thermometer and thermostatic bath 135 g (1 mole) of sulphuryl chloride are charged, cooled to 0° C. and 73.1 g (1 mole) of N,N-dimethylformamide are added under stirring yet maintaining the temperature below 5° C.

At the end of the addition the temperature is allowed to rise up to 20° C. and maintained constant for at least 3 hours.

208 g of $[SO_2Cl_2.(CH_3)_2NCHO]$ as a oily liquid are obtained.

EXAMPLE 3

Preparation of the hydrochloride of D(—)2-(p-hydroxyphenyl)glycyl chloride hemisolvate with dioxane In a flask equipped with stirrer, thermometer and thermostatic bath 50 g (0.3 mole) of D(—)2-(p-hydroxyphenyl)glycine are suspended in 150 ml dioxane; the suspension is treated at room temperature with gaseous HCl to give the hydrochloride of the aminoacid hemisolvate.

Upon cooling to 10° C. 75 g (0.39 mole) of adduct (I) prepared according to Example 1 are charged.

Once the addition is ended the mixture is heated up to 20°–30° C. for 15 minutes.

The reaction mass is cooled to 20° C. and optionally seeded with 500 mg of the previously obtained crystalline chlorinated compound. Once the crystallization is ended the mixture is cooled down to 0° C. to which 100 ml dichloromethane are added, and the crystallization is further allowed for 4 hours. The crystalline precipitate thus obtained is filtered, washed with dioxane and dichloromethane and dried under vacuum at 30° C.

About 60 g (0.225 mole) hydrochloride of D(—)2(p-hydroxyphenyl)glycyl chloride hemisolvate are obtained having an IR spectrum according to the standards and a titer of 93.5% without solvent.

EXAMPLE 4

Preparation of the hydrochloride of D(—)2(p-hydroxyphenyl)glycyl chloride hemisolvate with acetonitrile.

50 g of D(—)2(p-hydroxyphenyl)glycine are suspended in a solvent mixture of 50 ml dioxane and 100 ml acetonitrile, to which gaseous HCl is added at room temperature up to saturation thus obtaining the hydrochloride of the aminoacid solvate. 75 g of adduct (I) are slowly added at 10° C. and then heated up to 25° C. for 15 minutes.

The mixture is slowly cooled thus causing the spontaneous crystallization of the chlorinated product. The reaction mixture is maintained to 0° C. for 4 hours in order to complete the crystallization.

The compound is recovered by filtration, washed with acetonitrile and dried under vacuum. About 58 g of the desired chlorinated compound solvate with acetonitrile are obtained. The IR spectrum shows that the product has a high purity degree; titre without solvent: 96%.

EXAMPLE 5

Preparation of the hydrochloride of D(—)2(p-hydroxyphenyl)glycyl chloride hemisolvate with dioxane The process of Examples 3, 4 is repeated except that a mixture of solvents consisting of 100 ml dioxane and 50 ml $CH_2Cl_2$ was used. 60 g of hydrochloride of D(—)2(p-hydroxyphenyl)glycyl chloride hemisolvate are obtained. Titre without solvent: 94%. IR spectrum according to standards.

EXAMPLE 6

The process of Examples 3, 4, 5 is followed except that a mixture of solvents consisting of 100 ml dioxane and 50 ml benzene is used.

54 g of the desired chlorinated compound are obtained having a titre of 93.5% without solvent and an IR spectrum according to standards.

EXAMPLE 7

The process according to Examples 3, 4, 5, 6 is repeated except that a mixture consisting of 100 ml dioxane and 50 ml n-hexane is used.

54 g of the desired chlorinated compound are obtained having a titer of 92.5% without solvent and an IR spectrum according to standards.

EXAMPLE 8

The process of Examples 3 to 7 is repeated except that a mixture of solvents consisting of 100 ml dioxane and 100 ml ethyl acetate is used instead. 50 g of the desired chlorinated compound are obtained. The titre without solvent is 93% and the IR spectrum conforms to standards.

What we claim is:

1. A method for chlorinating the carboxylic group of an hydroxyphenylglycine essentially comprising the steps of:

suspending said hydroxyphenylglycine in at least one organic solvent;

treating the obtained suspension with gaseous HCl at room temperature to give the hydrochloride of said hydroxyphenylglycine;

chlorinating at 10° to 30° C. the said hydrochloride with an adduct of general formula $[XCl_2.R_1R_2NCHO]$ wherein X is SO or $SO_2$ and $R_1$ and $R_2$ are lower alkyl or aryl radicals.

2. The method of claim 1, wherein said hydroxyphenylglycine is 2-(p-hydroxyphenyl)glycine.

3. The method of claim 1, wherein said adduct is $[SOCl_2.(CH_3)_2NCHO]$.

4. The method of claim 1, wherein said at least one organic solvent is selected from the group consisting of dioxane and mixtures of dioxane and one or more further solvents such as dichloromethane, benzene, acetonitrile, chloroform, dichloroethane, n-hexane and ethyl acetate.

* * * * *